United States Patent [19]

Clasby, III

[11] Patent Number: 4,655,775

[45] Date of Patent: Apr. 7, 1987

[54] INTRAOCULAR LENS WITH RIDGES

[75] Inventor: Thomas J. Clasby, III, Laguna Beach, Calif.

[73] Assignee: American Hospital Supply Corporation, Evanston, Ill.

[21] Appl. No.: 665,040

[22] Filed: Oct. 26, 1984

[51] Int. Cl.$^4$ ............................................. A61F 2/16
[52] U.S. Cl. ..................................................... 623/6
[58] Field of Search .............................. 3/13, 1; 623/6

[56] References Cited

U.S. PATENT DOCUMENTS

| 4,110,848 | 9/1978 | Jensen | 3/13 |
|---|---|---|---|
| 4,122,556 | 10/1978 | Poler | 3/13 |
| 4,149,279 | 4/1979 | Poler | 3/13 |
| 4,159,546 | 7/1979 | Shearing | 3/13 |
| 4,244,060 | 1/1981 | Hoffer | 3/13 |
| 4,249,271 | 2/1981 | Poler | 3/13 |
| 4,298,995 | 11/1981 | Poler | 3/13 |
| 4,326,306 | 4/1982 | Poler | 3/13 |
| 4,340,979 | 7/1982 | Kelman | 3/13 |
| 4,366,582 | 1/1983 | Faulkner | 3/13 |
| 4,412,359 | 11/1983 | Myers | 3/13 |
| 4,468,820 | 9/1984 | Uhler et al. | 3/13 |
| 4,485,499 | 12/1984 | Castleman | 3/13 |
| 4,547,914 | 10/1985 | Castleman | 623/6 |

OTHER PUBLICATIONS

Medical Optics PC-15L Posterior Chamber Intraocular Lens, (advertisement) American Medical Optics, 2 pages, Oct. 1983.
"The Hoffer Ridge Lenses from Cilco", (advertisement) 6 pages, Cilco, Inc., 1616 13th Ave., Box 1680, Huntington, West Va., 25717, Mar. 1983.
*Intraocular Lens Implantation Techniques & Complications* (book) by H. M. Clayman et al, Publisher-The C. V. Mosby Co., St. Louis, Toronto, London (1983) pp. 148-151.
"Ovoid Optic Posterior Chamber Intraocular Lens: The First One Hundred Cases", *American Intra-Ocular Implant Society Journal*, Henry M. Clayman, M.D., vol. 8, No. 4, pp. 343-345, Fall 1982.
"The 'Soft J' Loop Posterior Chamber Lens", Cilco advertisement, 3/81.
"The Kratz 'Soft J' Loop Posterior Chamber Lens from Cilco", Cilco, date unknown.
"New The Model 150 Pearce Vaulted Y Posterior Chamber Lens", Coburn advertisement, dated unknown.
"Ridley Revisited: Anatomic and Lens Design Considerations in Posterior Chamber Pseubophakia", *Current Concepts in Cataract Surgery*, C. William Simcoe, The C. V. Mosby Company, St. Louis, Mo., 1980, pp. 133-143.

*Primary Examiner*—Ronald L. Frinks
*Attorney, Agent, or Firm*—Gordon L. Peterson

[57] ABSTRACT

An intraocular lens for implantation in the posterior chamber of the eye including an optic having a posterior surface and first and second ridges adjacent the periphery of the optic and projecting generally posteriorly from the posterior surface. The ridges are circumferentially spaced to define openings between the ridges. Fixation members are mounted on the optic for at least assisting in retaining the optic in the posterior chamber with the ridges in contact with the posterior capsule of the capsular bag to space the posterior surface of the optic from the posterior capsule. The fixation members have knees adjacent the periphery of the optic which facilitate insertion of the intraocular lens into the eye.

13 Claims, 4 Drawing Figures under# INTRAOCULAR LENS WITH RIDGES

BACKGROUND OF THE INVENTION

In cataract surgery, the natural lens is removed. To refocus the light on the retina and thus restore vision, an intraocular lens is implanted in place of the natural lens.

The intraocular lens can be implanted at various locations within the eye, such as within the capsular bag in the posterior chamber. After implantation of the intraocular lens in the capsular bag, it is sometimes necessary to perform a surgical technique known as discission in which an opening is formed in the posterior capsule. Discission has been performed with mechanical cutting instruments, such as a needle, and more recently, with a surgical laser. Discission may be necessary, for example, to restore vision that has become clouded following implantation of the intraocular lens.

A typical intraocular lens includes an optic and fixation members, with the optic having a flat posterior surface which seats against the posterior capsule. To avoid pitting of the posterior surface of the optic when discission is carried out with a surgical laser, it is necessary to space the posterior surface from the posterior capsule.

One way of spacing the posterior surface of the optic from the posterior capsule is to form an annulus on the posterior surface of the optic, and examples of such construction are shown in Shearing U.S. Pat. No. 4,159,546 and Hoffer U.S. Pat. No. 4,244,060. Alternatively, the posterior surface of the optic can be made concave so that the posterior periphery of the optic engages the posterior capsule with central regions of the posterior surface being spaced from the posterior capsule. Unfortunately, these annular posterior projections on the optic tend to hamper insertion of the intraocular lens into the eye. More specifically, the annular projection is difficult to slide across the iris and causes portions of the iris, in effect, to build up in front of the advancing projection.

The annular projections have other disadvantages. For example, they add weight to the intraocular lens and tend to inhibit the escape of tissue debris or cortical remnants. If the optic becomes decentered, the annular projection may cause visual aberrations. The annular projection may also enable wrinkles to form in the posterior capsule. Wrinkles are undesirable when discission is being carried out. Finally, gripping of the optic with forceps necessarily involves gripping of the annular projection, and this can cause structural failure of the projection.

SUMMARY OF THE INVENTION

This invention provides an intraocular lens which spaces the posterior surface of the optic from the posterior capsule and which overcomes or reduces the disadvantages noted above. This is accomplished by eliminating the annular projection of the prior art in favor of first and second circumferentially spaced ridges which project generally posteriorly from the posterior surface of the optic. These ridges stably support the optic, space the posterior surface of the optic from the posterior capsule and can serve as runners to facilitate insertion of the intraocular lens into the eye. The ridges are spaced circumferentially and define openings so the ridges tend to glide across the iris like runners rather than tending to cause portions of the iris to build up and impede insertion of the intraocular lens.

Because the ridges do not form an annulus, less material is required for the optic, and consequently, the weight of the optic is reduced as compared with an optic of equal diameter having the annular projections. Alternatively, the optic of this invention can have about the same weight as such a prior art optic and be of larger diameter.

The ridges are also useful in removing wrinkles which may tend to form in the posterior capsule. In this regard, the ridges engage the posterior capsule so that, when the optic is biased posteriorly by the fixation members, the ridges bear against the posterior capsule and tend to stretch the posterior capsule so as to eliminate or minimize wrinkles. Because the ridges are spaced circumferentially, there is no material between them to inhibit stretching of the posterior capsule. In addition, this circumferential spacing provides a space to permit the escape of cortical remnants, and this space is less likely to cause visual aberrations in case of decentering than would an annular projection.

The ridges are adjacent the periphery of the optic, and to facilitate manufacture, are preferably flush with portions of the periphery of the optic, respectively, where the ridges meet such portions of the periphery. Although the ridges could be discontinuous, they are preferably continuous and have opposite ends which are spaced apart to define openings between the ridges. The ridges and the posterior surface preferably cooperate to define a channel-like construction with the openings being on the opposite ends of the channel-like construction. When so constructed, the ridges are more likely to act like runners to facilitate insertion of the lens into the eye.

The ridges must be sufficiently long so that the axis of the optic will not tilt unacceptably relative to the optical axis of the eye when in use. On the other hand, the ridges should not be so long that they cannot act as runners to facilitate insertion of the intraocular lens into the eye. Although the circumferential length of the ridges can vary, a circumferential extent of about 71 degrees to about 79 degrees is preferred, and the middle of that range is considered optimum. Also, the ridges are preferably generally opposite of each other.

Another function which the ridges can serve is to mount, or assist in mounting, the fixation members. For this purpose, each of the ridges may have a radially thickened section for receiving an inner end portion of the associated fixation member.

Each of the fixation members can advantageously be in the form of a resilient, flexible strand. Another feature of this invention is the configuring of the strands to facilitate insertion of the intraocular lens behind the iris. This is accomplished by providing a knee at an appropriate location along each of the strands which deflects into a sharper bend or corner when the strand is deflected radially inwardly. This corner can then be positioned behind the iris with relative ease.

The invention, together with additional features and advantages thereof, may best be understood by reference to the following description taken in connection with the accompanying illustrative drawing.

DESCRIPTION OF THE PREFERRED EMBODIMENT

Figure 1:
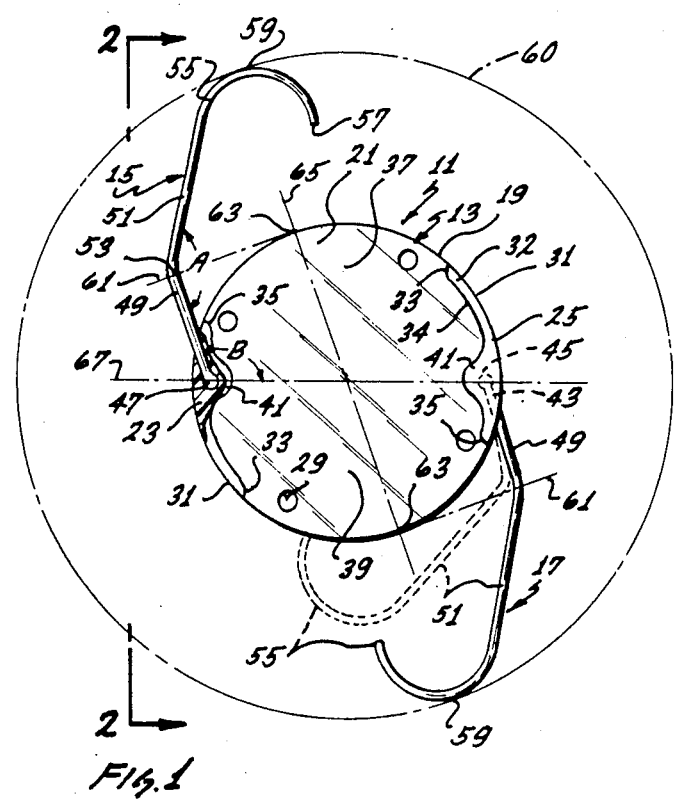
FIG. 1 is a rear elevational view of an intraocular lens constructed in accordance with the teachings of this invention.
Figure 2:
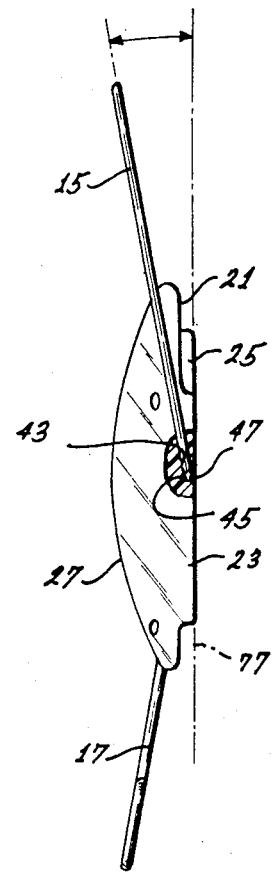
FIG. 2 is a side elevational view partially in section of the intraocular lens and taken along line 2—2 of FIG. 1.

FIGS. 1 and 2 show an intraocular lens 11 which is designed for use with extracapsular cataract extraction and which includes an optic 13 and fixation members in the form of strands 15 and 17. The optic 13 has a circular periphery 19, a planar, posterior surface 21 and identical ridges 23 and 25 projecting generally posteriorly from the posterior surface. The intraocular lens 11 is adapted to replace the natural lens of the human eye and the optic 13 may be, for example, a plano-convex lens of suitable diopter power. As such, the optic 13 has a convex anterior surface 27 (FIG. 2). The optic 13 may be constructed of a suitable, biocompatible material, such as polymethylmethacrylate. The optic 13 also has positioning apertures 29 adjacent the periphery 19. The optic 13 may be of relatively large diameter and may, for example, have a diameter of 6.5 millimeters.

The ridges 23 and 25 are spaced circumferentially and diametrically opposed. The ridges 23 and 25 need not be diametrically opposite but, preferably, central regions of the ridges are not offset by more than 35 and 38 degrees from being diametrically opposite. In the embodiment illustrated, each of the ridges 23 and 25 is continuous and extends circumferentially for about 75 degrees.

Each of the ridges 23 and 25 has an outer peripheral surface 31 which is generally cylindrical, of the same diameter as the optic 13 and flush with a portion of the periphery 19 of the optic. Each of the ridges 23 and 25 has a planar posterior surface 32, a curved inner surface 34 and opposite ends 33 and 35. As shown in FIG. 1, the ends 33 and 35 of the ridges 23 and 25 are spaced apart circumferentially to define circumferential openings 37 and 39. As such, the ridges 23 and 25 cooperate with the posterior surface 21 to define a channel-like construction, with the openings 37 and 39 being on the opposite ends of the channel-like construction. The openings 37 and 39 are sufficiently wide so that the ridges 23 and 25 can act as runners to facilitate insertion of the intraocular lens 11 into the eye.

The strands 15 and 17 are mounted on the optic 13 at the ridges 23 and 25, respectively, and for this purpose, each of the ridges has a radially thickened section 41. The radially thickened sections 41 are diametrically opposed and are located closer to the ends 35 than the ends 33 of the associated ridge 23 and 25. The sections 41 provide the necessary strength and dimensions for mounting of the strands 15 and 17.

Although the strands 15 and 17 can be mounted on the optic 13 in different ways, in the embodiment illustrated, a bore 43 is drilled into the periphery 19 at the ridges 23 and 25, and an axially extending cross bore 45 is drilled into each of the ridges 23 and 25 from the posterior surface 32. The bores 43 need not lie entirely within the associated ridges 23 and 25, and in the embodiment illustrated, each of the bores 43 opens partially anteriorly of the associated ridge as shown in FIG. 2. The bores 43 receive the inner end portions of the strands 15 and 17, and a hot rod (not shown) can be inserted into the cross bores 45 to melt the ends of the strands to form a head 47 which locks the strands to the associated ridge.

The strands 15 and 17 are identical, and although each of them may comprise one or more filaments, in this embodiment each of them is integrally constructed of a flexible, resilient material, such as polypropylene. Each of the strands 15 and 17 includes an inner section 49, an intermediate section 51 joined to the inner section at a knee 53 to form an obtuse angle "A" and an outer section 55 terminating in an outer end 57 joined to the distal end of the intermediate section. The inner sections 49 and the intermediate section 51 are linear, and in the unstressed condition, the sections 49 are parallel and the sections 51 are parallel. The outer sections 55 are approximately half circular. A location 59 on each of the outer sections 55 is at a maximum distance from the center of the optic 13 in the unstressed condition of the strands 15 and 17, and each of the locations 59 lies on a circle 60 having its center at the center of the optic.

In the illustrated embodiment, the strands 15 and 17 project anteriorly at a 10-degree angle as shown in FIG. 2. Thus, the strands 15 and 17 project generally radially of the optic 13.

The obtuse angle "A" may be of various sizes and, in the embodiment illustrated, is approximately 150 degrees. The angle "A" causes the intermediate section 51 to extend somewhat circumferentially of the optic 13 in a first circumferential direction partially across the associated opening, and the part-circular nature of the outer section 55 extends in such a direction as to cause the strand to extend circumferentially in that direction partially across the associated opening and ultimately loop back toward the optic. Thus, the inclination of the intermediate sections 51 and the curvature of the outer section 55 is such as to bring the strands 15 and 17 partially across the openings 37 and 39, respectively.

The strands 15 and 17 are resiliently deformable at the associated knees 53 such that the strands can be deflected inwardly to the dashed-line positions shown in FIG. 1. This materially reduces the obtuse angle to form the knee 53 into a much sharper bend. This is for the purpose of enabling the knee 53 to more easily get behind the iris during the lens insertion procedure.

The knee 53 is at a location along the associated strand which is no more than about one-third the distance along the strand from the optic to the periphery 19 to the location 59. Preferably, the knee 53 lies along a tangent 61 tangent to a peripheral location 63 which, in turn, is defined by the intersection of a diametral line 65 and the periphery 19. The diametral line 65 bisects the optic 13 between the inner sections 49, and in this embodiment, is parallel to the inner sections. The knee 53 can be at various locations along the tangent 61, and this is controlled by the angle at which the inner section 49 projects from the optic 13. In this embodiment, the inner ends of the strands 15 and 17 are diametrically opposed along a diametral line 67, and the inner sections 49 form an obtuse angle "B" with the diametral line 67. Although the angle "B" may vary widely, in this embodiment, it is approximately 110 degrees.

Figure 3:
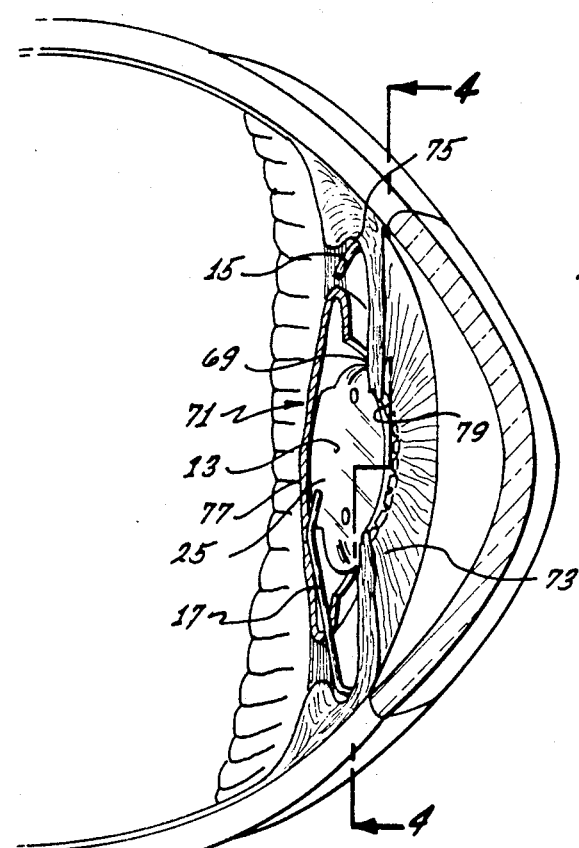
FIG. 3 is a sectional view through the human eye, with the intraocular lens implanted.
Figure 4:
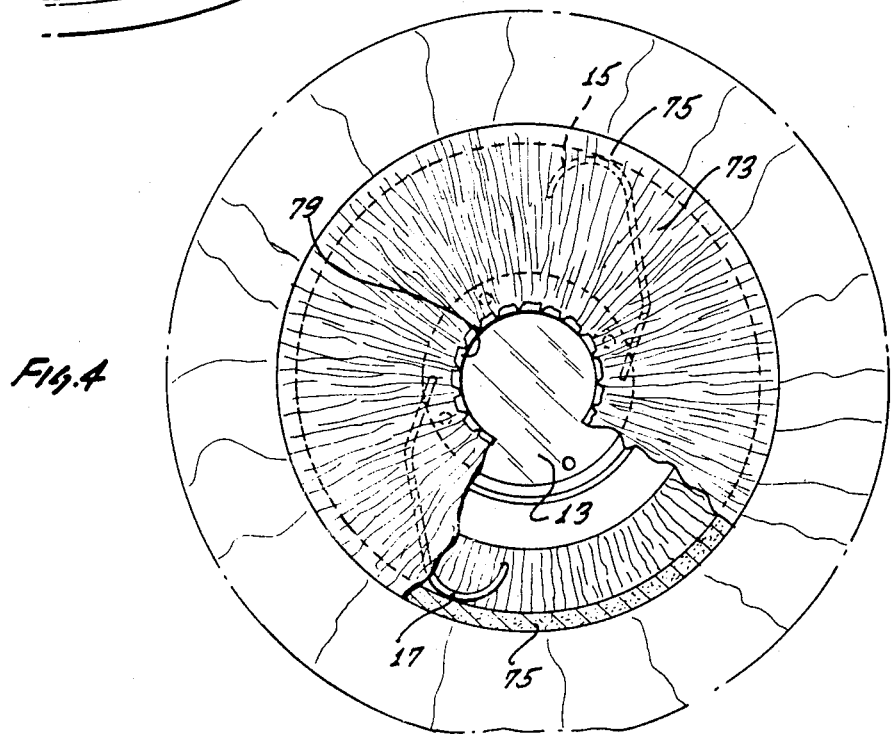
FIG. 4 is a sectional view taken generally along line 4—4 of FIG. 3.

The intraocular lens 11 is adapted to be implanted in the posterior chamber 69 following extracapsular extraction of the natural lens. FIGS. 3 and 4 show the intraocular lens implanted in the posterior chamber 69 with the optic 13 contacting the capsular bag 71 behind the iris 73. Although the intraocular lens 11 can be mounted within the capsular bag 71, as shown in FIG. 4, the strands 15 and 17 engage the ciliary sulcus 75 to retain the optic 13 in the posterior chamber 69. When so mounted, the strands 15 and 17 are resiliently deformed radially inwardly to retain the optic 13 essentially coaxial with the iris 73. The strands 15 and 17 resiliently urge the optic 13 posteriorly and urge the ridges 23 and 25 into contact with the posterior capsule 77 to space the posterior surface 21 anteriorly of the posterior capsule. This can also be seen in FIG. 2 where the posterior capsule 77 is represented by a broken line. Accordingly, discission can be carried out with a surgical laser without pitting the optic 13. In addition, the urging of the ridges 23 and 25 against the posterior capsule 77 tends to stretch the posterior capsule to remove wrinkles and to resist formation of new wrinkles. This wrinkle-inhibiting feature is particularly effective against wrinkles which extend generally transverse to a line between central regions of the ridges 23 and 25.

The intraocular lens 11 can be implanted in accordance with known techniques. However, the ridges 23 and 25 can be used as runners so the intraocular lens can glide through the incision formed in the eye for implantation purposes and across the iris 73. Thus, the direction of insertion should be generally parallel to the ridges 23 and 25. When gripping the lens 11 with forceps, the forceps can grip the optic 13 between the ridges 23 and 25 so there is no danger of the forceps causing structural failure of the ridges.

During the implantation procedure, the intraocular lens is slid along the iris 73, and when the knee 53 of the trailing strand is near the aperture 79 of the iris 73, the trailing strand is deflected radially inwardly by the surgeon generally to the dashed-line position of FIG. 1 to form the knee 53 into a sharper bend which facilitates placement of such knee through the opening 79 and behind the iris 73.

Although an exemplary embodiment of the invention has been shown and described, many changes, modifications and substitutions may be made by one having ordinary skill in the art without necessarily departing from the spirit and scope of this invention.

I claim:

1. An intraocular lens for implantation in the posterior chamber of the eye, said intraocular lens comprising:
    an optic having a posterior surface, a periphery and first and second ridges adjacent the periphery and projecting generally posteriorly from the posterior surface;
    each of said first and second ridges having opposite ends, said first and second ridges being circumferentially spaced to define first and second openings between the ridges;
    fixation means mounted on the optic for at least assisting in retaining the optic in the posterior chamber with the ridges in contact with the posterior capsule of the capsular bag to space the posterior surface of the optic from the posterior capsule;
    said ridges being sufficiently short and being spaced apart sufficiently so that they can act as runners to facilitate insertion of the intraocular lens into the eye; and
    said ridges being essentially flush with portions of the periphery of the optic, respectively, where said ridges meet such portions of the periphery.

2. An intraocular lens as defined in claim 1 wherein said ridges are generally opposite each other.

3. An intraocular lens as defined in claim 1 wherein said fixation means includes a first resilient member projecting from the optic and extending across at least a portion of said first opening in the unstressed condition of said first fixation member.

4. An intraocular lens as defined in claim 1 wherein the optic has a circular periphery and each of the ridges has a generally cylindrical peripheral surface and a planar posterior surface.

5. An intraocular lens as defined in claim 1 wherein said fixation means includes first and second flexible resilient fixation members at least partially mounted, respectively, on the first and second ridges.

6. An intraocular lens as defined in claim 5 wherein said first ridge has a radially thickened section and an inner end portion of the first fixation member is received within the radially thickened section.

7. An intraocular lens as defined in claim 1 wherein each of said ridges extends for about 71 to about 79 degrees.

8. An intraocular lens as defined in claim 1 wherein said ridges and said posterior surface cooperate to define a channel-like construction with said first and second openings being on the opposite ends of said channel-like construction.

9. An intraocular lens as defined in claim 1 wherein each of said ridges is continuous.

10. An intraocular lens as defined in claim 1 wherein said fixation means includes a first resilient strand mounted on said optic, said first strand having an inner section, an intermediate section joined to the inner section at a knee to form an obtuse angle and an outer section terminating in an outer end and joined to the distal end of the intermediate section, said first strand being resiliently deformable at said knee to materially reduce said obtuse angle to form said knee into a sharper bend whereby insertion of the intraocular lens into the eye is facilitated.

11. An intraocular lens as defined in claim 10 wherein said fixation means includes a second resilient strand mounted on said optic and having an inner section, an intermediate section joined to the inner section at a knee to form an obtuse angle and an outer section terminating in an outer end and joined to the distal end of the intermediate section, said optic being generally circular, a diametral line through the optic bisecting the optic between said inner sections intersecting the periphery of the optic at a peripheral location and a tangent through said periphery at said peripheral location extending through or closely adjacent the knee of the first strand.

12. An intraocular lens for implantation in the eye comprising:
    an optic having a periphery;
    first and second resilient flexible strands mounted on the optic and projecting generally radially outwardly of the periphery of the optic;
    said first strand having an inner section, an intermediate section joined to the inner section at a knee to form an obtuse angle and an outer section terminating in an outer end and joined to the distal end of the intermediate section, said first strand being resiliently deformable at said knee to materially reduce said obtuse angle to form said knee into a sharper bend whereby insertion of the intraocular lens into the eye is facilitated;
    a location on said outer section being at a maximum distance from the center of the optic in the unstressed condition of said first strand;

said knee being at a location along said first strand which is no more than about one-third the distance along the strand from the optic periphery to said location on said outer section; and a second resilient strand mounted on said optic and having an inner section, an intermediate section joined to the inner section at a knee to form an obtuse angle and an outer section terminating in an outer end joined to the distal end of the intermediate section, said optic being generally circular, a diametral line through the optic bisecting the optic between said inner sections intersecting the periphery of the optic at a peripheral location and a tangent to said periphery at said peripheral location extending through or closely adjacent the knee of the first strand.

13. An intraocular lens as defined in claim 12 wherein said inner sections are generally linear and generally parallel and said diametral line is generally parallel to said inner section.

* * * * *